US010230328B2

(12) United States Patent
Nos Aguila et al.

(10) Patent No.: US 10,230,328 B2
(45) Date of Patent: Mar. 12, 2019

(54) METHOD AND SYSTEM FOR MONITORING THE QUALITY OF PHOTOVOLTAIC CELLS

(71) Applicant: COMMISSARIAT A L'ENERGIE ATOMIQUE ET AUX ENERGIES ALTERNATIVES, Paris (FR)

(72) Inventors: Oriol Nos Aguila, Grenoble (FR); Wilfried Favre, Chambéry (FR); Fabien Ozanne, Allevard (FR); Pierre-Jean Ribeyron, Saint Ismier (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 167 days.

(21) Appl. No.: 15/105,424

(22) PCT Filed: Dec. 19, 2014

(86) PCT No.: PCT/EP2014/078626
§ 371 (c)(1),
(2) Date: Jun. 16, 2016

(87) PCT Pub. No.: WO2015/091895
PCT Pub. Date: Jun. 25, 2015

(65) Prior Publication Data
US 2016/0322934 A1    Nov. 3, 2016

(30) Foreign Application Priority Data
Dec. 19, 2013    (FR) .................................... 13 63105

(51) Int. Cl.
H02S 50/15    (2014.01)
G01N 21/64    (2006.01)
(Continued)

(52) U.S. Cl.
CPC ......... *H02S 50/15* (2014.12); *G01N 21/6489* (2013.01); *G01N 21/95* (2013.01);
(Continued)

(58) Field of Classification Search
CPC ............... G01N 21/6489; G01N 21/95; G01N 21/9501; G01N 2201/12;
(Continued)

(56) References Cited

U.S. PATENT DOCUMENTS

2005/0285129 A1* 12/2005 Jackson, III ....... G01N 21/6456
257/98
2009/0206287 A1*  8/2009 Trupke ............... G01N 21/6489
250/582
(Continued)

FOREIGN PATENT DOCUMENTS

WO    2009/129575 A1    10/2009

OTHER PUBLICATIONS

Hallam et al., "Photoluminescence Imaging for Fast Determination of the Implied Open Circuit Voltage of Silicon Wafers", 24th European Photovoltaic Solar Energy Conference, Sep. 21-25, 2009, pp. 2015-2018; cited in French Search Report.
(Continued)

*Primary Examiner* — David Porta
*Assistant Examiner* — Blake Riddick
(74) *Attorney, Agent, or Firm* — Westerman, Hattori, Daniels & Adrian, LLP

(57) ABSTRACT

A method and system for monitoring the quality of photovoltaic cells is described, the method including for each cell: an excitation step, during which the cell to be monitored is subjected to excitation at a predetermined level of excitation; a step of acquiring at least one luminescence image of the cell to be monitored after excitation; and a step of processing the acquired image. The invention is character-
(Continued)

ized in that, for each cell, there is provided a preliminary step for determining an excitation level adjusted to the cell, the respective adjusted excitation levels of the different cells to be monitored being adapted such that the luminescence intensities of the signals emitted by the different cells are equal at a given reference luminescence intensity.

15 Claims, 7 Drawing Sheets

(51) Int. Cl.
    *G01N 21/95*     (2006.01)
    *G06T 5/50*     (2006.01)
    *H01L 21/66*     (2006.01)

(52) U.S. Cl.
    CPC ........... *G01N 21/9501* (2013.01); *G06T 5/50* (2013.01); *G01N 2201/12* (2013.01); *G06T 2207/10004* (2013.01); *H01L 22/12* (2013.01)

(58) Field of Classification Search
    CPC . G06T 2207/10004; G06T 5/50; H01L 22/12; H02S 50/15
    USPC .... 250/206, 208.1, 214 R, 458.1, 459.1, 582
    See application file for complete search history.

(56) References Cited

U.S. PATENT DOCUMENTS

| | | | |
|---|---|---|---|
| 2010/0084012 A1* | 4/2010 | Ribeyron | H01L 31/065 136/255 |
| 2011/0025839 A1* | 2/2011 | Trupke | G01N 21/6489 348/87 |
| 2011/0117681 A1* | 5/2011 | Bardos | C23C 16/52 438/7 |
| 2011/0234790 A1* | 9/2011 | True | G01N 21/6489 348/126 |
| 2012/0142125 A1 | 6/2012 | Trupke et al. | |
| 2012/0181452 A1* | 7/2012 | Trupke | G01N 21/6489 250/459.1 |
| 2012/0203494 A1* | 8/2012 | Haunschild | G01N 21/6489 702/117 |
| 2012/0288985 A1* | 11/2012 | Moriceau | H01L 21/30604 438/87 |
| 2012/0291861 A1* | 11/2012 | Mur | H01L 31/0745 136/255 |
| 2013/0062536 A1* | 3/2013 | Bardos | G01N 21/6489 250/459.1 |
| 2014/0039820 A1* | 2/2014 | Trupke | H02S 50/10 702/65 |

OTHER PUBLICATIONS

Michl et al., "Suns-PLI as a powerful tool for spatially resolved fill factor analysis of solar cells", Progress in Photovoltaics: Research and Applications; vol. 22, 2014, pp. 581-586; cited in the French Search Report and in the Specification.

Bakowskie et al., "Comparison of Recombination Active Defects in Multicrystalline Silicon by Means of Photoluminescence Imaging and Reverse Biased Electroluminescence", 26th European Photovoltaic Solar Energy Conference and Exhibition, Oct. 13, 2011, pp. 1839-1842; cited in the ISR.

Ferreira et al., "ImageJ User Guide", IJ 1.46r, Oct. 2, 2012, 198 pages; cited in the ISR.

Lin et al., "Automatic Detection of Internal defects in Solar Cells", IEEE, May 10, 2011, 4 pages; cited in the ISR.

Augarten et al., "Progress in Photovoltaics: Research and Applications", Prog. Photovolt: Res. Appl., vol. 21; 2013, pp. 933-941.

Johnston et al., "Correlations of Cu(In, Ga)Se2 imaging with device performance, defects, and microstructural properties", Journal of Vacuum Science and Technology A, vol. 30, No. 4, Jul.-Aug. 2012, pp. 04D111-1-04D111-6.

International Search Report and Written Opinion dated Jun. 10, 2015 issued in corresponding application No. PCT/EP2014/078626; w/ English partial translation and partial machine translation (34 pages).

French Search Report and Written Opinion dated Aug. 11, 2014 issued in counterpart application No. FR1363105; w/ English partial translation and partial machine translation (20 pages).

\* cited by examiner

METHOD AND SYSTEM FOR MONITORING THE QUALITY OF PHOTOVOLTAIC CELLS

The present invention concerns a method and a system for monitoring the quality of photovoltaic cells, for example, by photoluminescence or by electroluminescence.

A photoluminescence image of a photovoltaic cell, acquired after an excitation of the cell by a light beam, makes it possible to locate defects which may harm the performance of the cell. These defects appear in the image as darker zones than the image background. Different methods propose using the photoluminescence images to determine parameters of the cell, especially to identify and/or quantify the defects present in the cell.

The document "*Calculation of quantitative shunt values using photoluminescence imaging*", Augarten Y., Trupke T., Lenio M., Bauer J., Weber J. W., Juhl M. Kasemann M., Breitenstein O. (Prog. Photovolt.: Res. Appli., 21: 933-941. Doi: 10.1002/pip.2180 (2013)) proposes a method of quantification of current losses due to defects present in a cell based on photoluminescence images of the cell. The document "*Suns-PLI as a powerful tool for spatially resolved fill factor analysis of solar cells*" Mchl B., Impera D., Bivour M., Warta W., Schubert M. C. (Prog. Photovolt.: Res. Appl. Doi 10.1002/pip.2293 (2012)) describes a method of determination of a voltage open circuit (VOC) map and a pseudo-form factor (PFF) map of a silicon cell from photoluminescence intensities measured for the pixels of a photoluminescence image of the cell. Finally, the document "*Correlations of Cu(In,Ga)Se2 imaging with device performance, defects and microstructural properties*" Johnston S. et al. (J. Vac. Sci. Technol. A 30, 04D111 (2012)) studies the correlation between a mean luminescence intensity of a Cu(In,Ga)Se2 cell, determined from luminescence images of the cell, and on the one hand an open circuit voltage of the cell, and on the other hand a form factor of the cell.

In the existing methods, the photoluminescence images of the photovoltaic cells to be monitored are obtained by exciting the cells by monochromatic (laser) illumination with a fixed luminous power density and for a predefined period. The results obtained, however, are not entirely satisfactory because, depending on the cell analysed, its defects are more or less detectable in the photoluminescence images.

The present invention intends to improve the situation.

Accordingly, the invention concerns a method for monitoring the quality of a plurality of photovoltaic cells, involving for each cell:
an excitation step, during which the cell to be monitored is subjected to an excitation with a determined excitation level;
a step of acquisition of at least one luminescence image of the cell to be monitored after excitation;
a step of processing of the acquired image;
characterized in that there is provided, for each cell, a preliminary step of determination of an excitation level adjusted to that cell, the respective adjusted excitation levels of the different cells to be monitored being adapted so that the luminescence intensities of the signals emitted by the different cells are equal to an identical reference luminescence intensity.

The invention thus consists in adapting the excitation levels applied to the different photovoltaic cells to be monitored so that all the cells are placed at the same level, in terms of their luminescence response. Thanks to this, one greatly limits the risk of under-estimating or over-estimating the defects from one cell to another. The processing of the luminescence images obtained after excitation of the cells to be monitored at the adjusted excitation levels makes it possible to perform a quality monitoring which is consistent between the different cells, reliable and precise.

In one particular embodiment, during the preliminary step of determining the excitation level adjusted to the cell:
one measures the luminescence intensity emitted by the cell in response to an initial chosen excitation level;
one determines the excitation level adjusted to the cell from the measured luminescence intensity, the reference luminescence intensity, and data on the change in a luminescence response of a cell as a function of the excitation level applied to that cell.

The cell to be monitored is initially excited with an initial chosen excitation level. The luminescence intensity of the photon signal emitted by a cell in response to this initial excitation is measured in order to calculate a ratio between the measured intensity and the reference intensity. Based on this ratio, and taking into account the initial applied excitation level and the known change in the luminescence intensity of a cell as a function of the excitation level, one determines the adjusted excitation level to be applied to the cell so that its luminescence response is equal to the reference intensity.

Advantageously, one calculates a ratio of intensities between the reference luminescence intensity and the measured luminescence intensity and, the data on the change in the luminescence response as a function of the applied excitation level being normalized for the initial chosen excitation level, one directly obtains the excitation level adjusted to the cell with the help of said change data, based on said ratio of intensities taken as the luminescence intensity.

In this way, one determines the adjusted excitation level in a simple and rapid manner, without supplemental calculation.

Again advantageously, the cells to be monitored being manufactured by a production line, a learning phase is specified, during which:
one measures the open circuit voltages of a plurality of learning cells manufactured on said production line;
one determines a reference open circuit voltage, contained within a range defined by a mean of the measured open circuit voltages more or less than two times the standard deviation of the distribution of the measured open circuit voltages;
one determines the reference luminescence intensity from the reference open circuit voltage determined and for the initial chosen excitation level.

In this way, the reference luminescence intensity is adapted to the production line of the cells to be monitored.
In one particular embodiment, during the learning phase one subjects the learning cells to the initial chosen excitation level and measures the luminescence intensities of the learning cells in response to the excitation;
one determines the data on the change in the luminescence intensity of the learning cells subjected to the initial chosen excitation level as a function of the open circuit voltage of said learning cells.

By a learning process, one can thus determine data on the variation in the luminescence intensity of the cells as a function of their open circuit voltage and select a reference luminescence intensity based on this data.

Advantageously, for each cell to be monitored, the luminescence image of that cell being composed of a set of pixels to which respective luminescence intensity values are assigned, during the processing step:

one decomposes the luminescence image of the cell to be monitored into a first image corresponding to that cell without defects and a second image corresponding to defects of that cell, one calculates a mean of the luminescence intensity values associated with the pixels of the second image in order to determine a parameter for quantification of the defects of the cell.

Following the adjusted excitation of the cell to be monitored, a luminescence response image of the cell is acquired and then decomposed into two secondary images corresponding respectively to the image background and to the defects of the cell. From the secondary image containing the defects of the cell, one can construct a mean of the luminescence intensities of the pixels and thus determine a parameter for quantification of the defects.

Again advantageously, the parameter for quantification of the defects is corrected by a correction factor determined from a mean of the pixel values of the first image.

Due to the adjustment of the excitation levels applied to the cells to be monitored, the image backgrounds should ideally all be identical. However, due to adjustment errors in particular, slight deviations are possible. The result is an under-estimation or an over-estimation of the defects. To correct this, the defect quantification parameter is weighted by a correction factor determined from the mean value of luminescence intensity of the background image.

In one particular embodiment, during a learning phase, one determines correlation data between a parameter for loss of form factor and the defect quantification parameter, for the learning cells.

In this case, advantageously, for each cell to be monitored, one evaluates a parameter of loss of form factor of that cell based on the defect quantification parameter which has been determined and said correlation data.

Thus, based on the defect quantification parameter of a cell to be monitored, one can estimate the impact of the defects on the form factor. More precisely, with the help of correlation data between the defect quantification parameter and a loss of form factor, obtained by a learning process, and based on the defect quantification parameter determined for the cell to be monitored, one can evaluate a loss in the form factor of the cell which is produced by the defects.

Again advantageously, for each cell to be monitored, before or after, a step of metallization of that cell is carried out during the manufacturing process.

In this way, one can halt the production of defective cells, especially prior to metallization, and thus economize on metal.

The mode of excitation of the cell to be monitored can be a light beam or an electric current.

The invention also concerns a system for monitoring the quality of a plurality of photovoltaic cells comprising hardware and software means for implementing the steps of the method just defined.

In one particular embodiment, the system comprises:
an excitation device adapted to apply to a cell to be monitored an excitation with a determined excitation level;
a device for acquisition of a luminescence image of the cell after excitation;
an image processing module;
and it is characterized in that it comprises a module for determination of excitation levels adjusted to the cells to be monitored, said module being designed to adjust the respective excitation levels of the cells to be monitored so that the luminescence intensities emitted by said cells are equal to an identical reference luminescence intensity.

The system can comprise all or some of the following additional characteristics:
the module for determination of excitation levels adjusted to the cells to be monitored is designed to determine the excitation level adjusted for a cell to be monitored from a measured luminescence intensity of said cell in response to an initial chosen excitation level, the reference luminescence intensity, and data on the change in a luminescence response of a cell as a function of the excitation level applied to that cell;
it comprises a learning module designed to determine
a reference open circuit voltage, from measured open circuit voltages of learning cells, said reference open circuit voltage being contained within a range defined by a mean of the measured open circuit voltages more or less than two times the standard deviation of the distribution of the measured open circuit voltages, and
the reference luminescence intensity from the reference open circuit voltage determined and for the initial chosen excitation level;
the image processing module is adapted to decompose the luminescence image of a cell to be monitored, acquired after excitation of said cell at the adjusted excitation level, into a first image corresponding to said cell without defects and a second image corresponding to defects of said cell, and it comprises a module for determination of a parameter for quantification of defects of the cell to be monitored, designed to calculate a mean of the luminescence intensity values associated with the pixels of the second image;
it comprises a module for evaluation of a parameter of loss of form factor of a cell to be monitored from the determined parameter for quantification of the defects of said cell and data on the correlation between the parameter of loss of form factor and the defect quantification parameter.

The invention also concerns a method for monitoring the quality of a plurality of photovoltaic cells, involving for each cell:
an excitation step, during which the cell to be monitored is subjected to an excitation;
a step of acquisition of at least one luminescence image of the cell to be monitored after excitation;
a step of processing of the acquired image;
characterized in that, for each cell to be monitored, during the processing step, one decomposes the luminescence image of the cell into a first image corresponding to that cell without defects and a second image corresponding to defects of that cell.

Advantageously, to decompose the luminescence image of the cell to be monitored, the luminescence image of that cell being composed of a set of pixels to which respective luminescence intensity values are assigned:
one selects a plurality of pixels of said luminescence image;
one assigns to each of the selected pixels a value which is representative of a local environment of said pixel;
one assigns a new value to each pixel of the image from the values of the selected pixels in order to obtain a first image corresponding to the cell without defects;
one determines a second image corresponding to the defects of said cell based on the luminescence image and the first image.

Again advantageously, one calculates a mean of the luminescence intensity values associated with the pixels of the second image in order to determine a parameter for quantification of the defects of the cell.

The method advantageously involves some or all of the following additional characteristics:
one obtains said second image by forming a ratio or a subtraction between the luminescence image of the cell and the first image;
one assigns a new value to each pixel of the image by interpolation of the values of the selected pixels;
the defect quantification parameter is corrected by a correction factor determined from a mean of the pixel values of the first image;
the selected pixels of the luminescence image are situated at periodically spaced-apart locations.

Finally, the invention concerns a system for monitoring the quality of a plurality of photovoltaic cells, comprising:
an excitation device adapted to apply an excitation to a cell to be monitored;
a device for acquisition of a luminescence image of the cell after excitation;
an image processing module;
characterized in that the image processing module is adapted to decompose the luminescence image of each cell to be monitored into a first image corresponding to that cell without defects and a second image corresponding to defects of that cell.

The image processing module is advantageously designed to select a plurality of pixels of said luminescence image, assign to each of the selected pixels a value which is representative of a local environment of said pixel, assign a new value to each pixel of the image from the values of the selected pixels in order to obtain the first image, determine the second image from the luminescence image and the first image.

The image processing module is moreover advantageously designed to calculate a mean of the luminescence intensity values associated with the pixels of the second image in order to determine a parameter for quantification of the defects of the cell.

The invention will be better understood with the aid of the following description of a particular embodiment of the method and the system for monitoring the quality of a plurality of photovoltaic cells of the invention, referring to the attached drawings in which.

Figure 1:
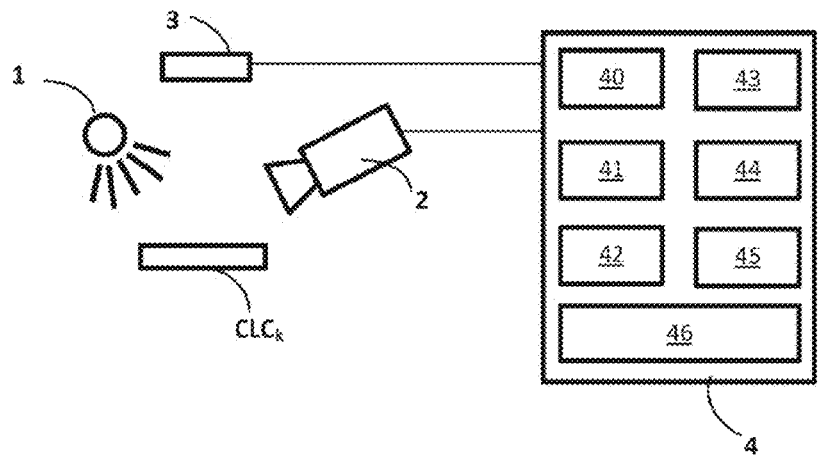
FIG. 1 shows the quality monitoring system according to one particular embodiment of the invention.

The quality monitoring method of the invention makes it possible to monitor the quality of photovoltaic cells being manufactured on a production line L, in order to detect, if appropriate, one or more cells having inadequate performance as compared to the desired performance.

The quality monitoring is implemented by a system comprising:
an excitation device 1, intended to excite a photovoltaic cell to emit photons by luminescence,
a device 2 for acquisition of luminescence images, such as a camera, designed to acquire digital images representative of the photons emitted by a photovoltaic cell in response to an excitation, in other words, images of the luminescence response of the cell after an excitation,
a sensor 3 to measure the luminescence intensity, adapted to measure the luminescence intensity of a signal of photons emitted by a photovoltaic cell after excitation,
a control device 4.

The quality monitoring system comprises hardware and software means to implement the steps of the method described below.

The control device 4 comprises in particular a central unit (not shown), in the present case a microprocessor, and various software modules:
a learning module 40, able to control the execution of the steps of a learning phase,
a module 41 for determination of an excitation level adjusted for a photovoltaic cell,
a module 42 for image processing and determination of a parameter for quantification of defects of a photovoltaic cell,
a module 43 for evaluation of a parameter of loss of form factor,
a module 44 for cell selection.

The control device 4 moreover comprises a storage memory 45, in particular to save the data obtained during the learning phase, and a man-machine interface 46 (screen, keyboard, etc.).

In the sample embodiment described here, the mode of excitation of the photovoltaic cells is a laser light beam. The excitation device 1 is a source of laser emission. In a variant, one could use another type of light beam or an excitation by electric current.

The photovoltaic cells are, for example, silicon heterojunction (SHJ) cells or solar cells. However, one could contemplate the application of the invention to any other type of photovoltaic cell. For example, one could mention silicon homojunction cells, thin layer cells based on amorphous silicon or other semiconductors such as CdTe (cadmium telluride), CuInGaSe (copper-indium-gallium selenide) or GaAs (gallium arsenide) cells or even multijunction cells.

The method involves an initial learning phase of the production line L, described hereinafter.

Learning Phase:

The learning phase makes it possible to determine various parameters regarding the photovoltaic cells produced by the production line L, namely:
data on the change in the luminescence intensity of photovoltaic cells produced by the production line L as a function of an open circuit voltage (curve $C_1$);
a reference value, or target, of the luminescence intensity, noted as $I_{PL,ref}$ for the photovoltaic cells to be monitored;

data on the change in the luminescence response of a photovoltaic cell as a function of the excitation level applied to it (curve $C_2$);

data on the correlation between a parameter GL for quantification of defects of a photovoltaic cell and a parameter of loss of form factor of that cell;

a threshold $TSH_{GL}$ of the defect quantification parameter.

The learning phase involves a first step E00 of fabrication of a batch of N photovoltaic cells, known as the "learning cells", noted as $CLA_1$, $CLA_2$, ..., $CLA_i$, ..., $CLA_N$, by the production line L. For example, the number N can be of the order of several hundred or even several thousand cells, depending on the degree of precision desired (representative sample).

Steps E01 to E06 make it possible to determine the curve $C_1$ and the reference luminescence intensity $I_{PL,ref}$.

In known fashion, a photovoltaic cell is characterized by an open circuit voltage "$V_{oc}$", corresponding to the voltage on the terminals of the cell when no current I is flowing (I=0). A production line generally produces cells whose respective voltages $V_{oc}$ can vary slightly from one cell to another. Typically, the voltages $V_{oc}$ of one batch of photovoltaic cells produced by a production line are distributed in a Gaussian distribution about a mean value $\overline{V_{oc}}$ and with a given standard deviation σ.

During step E01, the open circuit voltage $V_{oc\_i}$ of each of the learning cells $CLA_i$ is measured in a known fashion.

During step E02, one calculates a mean open circuit voltage value $\overline{V_{oc}}$ from the voltages $V_{oc\_i}$ measured for the cells $CLA_1$ to $CLA_N$.

One then measures the photoluminescence responses of each of the learning cells $CLA_1$ to $CLA_N$ when they are subjected to an excitation laser beam, with a chosen level of illumination, by means of the laser emission device 1. In the example described here, one selects a level of illumination equal to 40% of the maximum laser emission power of the laser emission device 1, the maximum laser power density being of the order of 120 mW/cm², and a duration of emission of the laser beam of the order of 10 ms. One could select a different level of illumination, but adapted in any case so that the photoluminescence responses of the photovoltaic cells do not saturate the acquisition device 2. We note as $P_{init}$ this initial chosen illumination level. In a variant, to obtain the desired level of illumination, one could select a fixed laser power density (such as 40% of the maximum power) and adjust the level of illumination by varying the duration of the excitation time of the cell, that is, the duration of the laser beam emission.

In order to measure the photoluminescence responses of the cells at the initial chosen illumination level $P_{init}$, during step E03, one subjects each learning cell $CLA_i$, with the index i being initially equal to 1, to a laser beam, the laser device 1 being tuned to a chosen power of 40% of its maximum emission power.

During step E04, one measures the photoluminescence intensity $I_{PL\_i}$ of the signal emitted by the learning cell $CLA_i$ in response to the laser excitation applied during step E03.

For a given level of illumination, it is known that the photoluminescence intensity $I_{PL}$ of a photovoltaic cell depends on the open circuit voltage $V_{oc}$ of that cell. More precisely, the intensity $I_{PL}$ is proportional to $$\left(\frac{eV_{oc}}{kT}\right).$$

In other words, we have the following relation:

$$I_{PL} \propto \exp\left(\frac{eV_{oc}}{kT}\right) \quad (1)$$

where:
e represents the elemental charge;
k represents the Boltzmann constant, and
T represents the temperature.

Figure 4A:
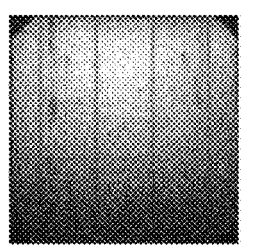
FIG. 4A shows a luminescence image relative to a photovoltaic cell to be monitored.
Figure 4B:
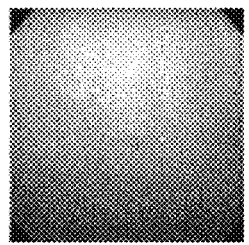
FIGS. 4B and 4C show two images obtained by decomposition of the image of FIG. 4A.
Figure 4C:
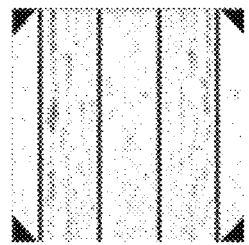
Figure 5A:
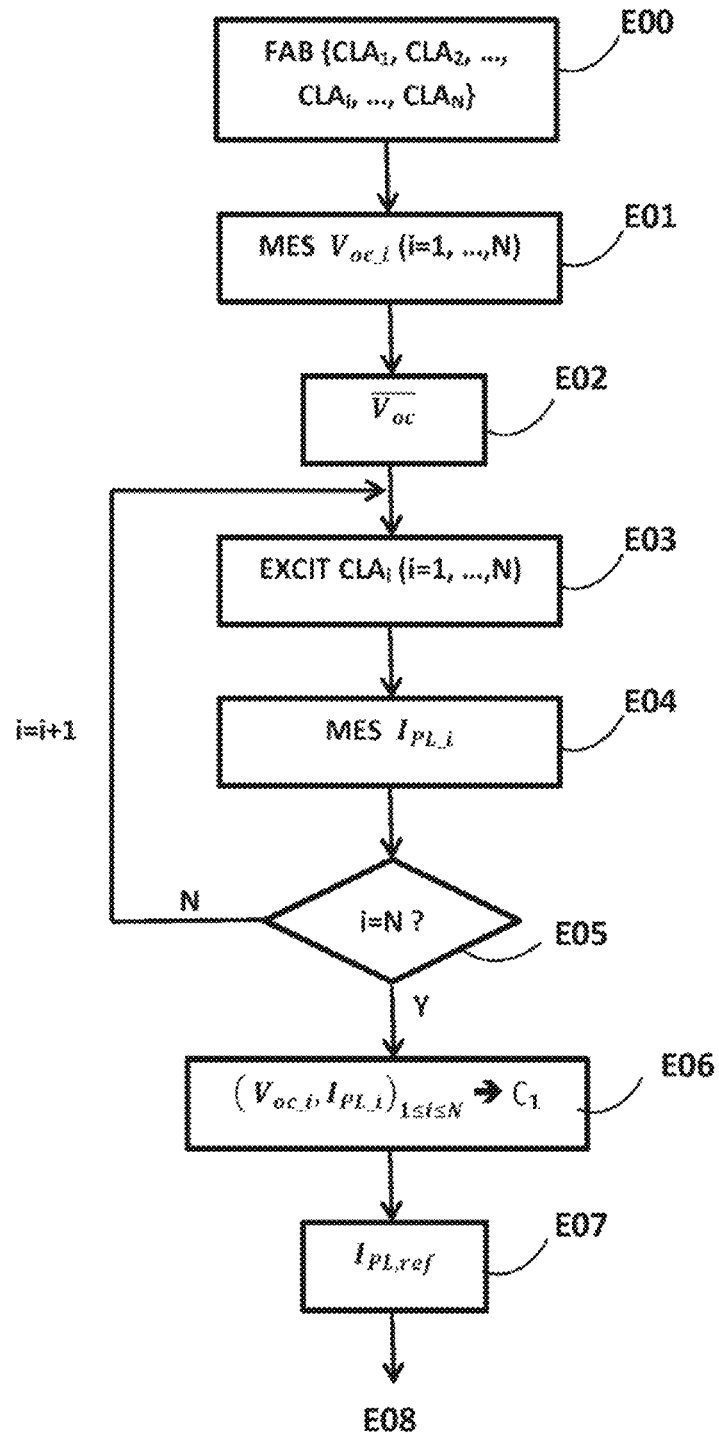
FIGS. 5A and 5B show steps of a learning phase of the method, according to one particular embodiment.

Steps E03 and E04 are repeated for each of the learning cells $CLA_i$, the index i ranging from 1 to N. A test step E05 is provided so that the method returns to step E03 if the index i is less than N (branch N in FIG. 4). When the photoluminescence responses of all the cells CLAi, with i ranging from 1 to N, have been measured, the method moves on to step E06 (branch Y in FIG. 5A).

At the end of step E05, one has for each learning cell $CLA_i$ (with i between 1 and N) a pair of measured values ($V_{oc\_i}$, $I_{PL\_i}$), each one containing the measured open circuit voltage $V_{oc\_i}$ and the photoluminescence intensity $I_{PL\_i}$ the cell $CLA_i$ measured in response to a chosen illumination equal to 40% of the maximum laser emission power of the device 1.

Figure 3:
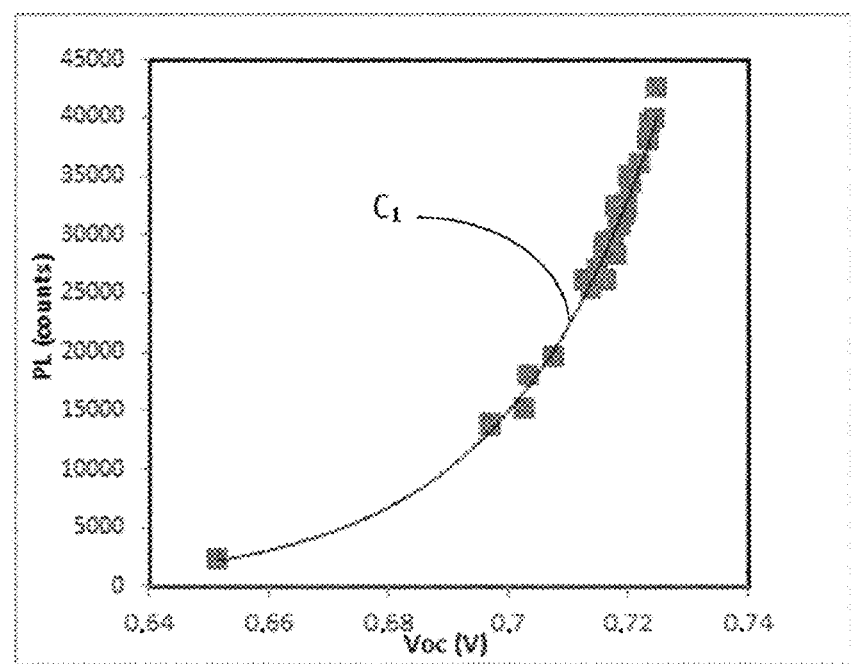
FIG. 3 shows data on the change in the luminescence intensity of photovoltaic learning cells as a function of the open circuit voltages of these cells.

During step E06, using the pairs ($V_{oc\_i}$, $I_{PL\_i}$) and taking into account the known proportionality relation (1), the control device 4 determines first data on the change in the photoluminescence intensity $I_{PL}$ as a function of the open circuit voltage $V_{oc}$ for the learning cells. These first change data form the curve $C_1$ as represented in FIG. 3. This curve $C_1$ is thus determined from learning data constituted by the pairs ($V_{oc\_i}$, $I_{PL\_i}$) and the relation (1).

During a step E07, the control device 4 determines the reference value of the photoluminescence intensity $I_{PL,ref}$ from a reference open circuit voltage value $V_{oc,ref}$ and with the aid of the curve $C_1$. In the sample embodiment described here, the reference open circuit voltage $V_{oc,ref}$ is chosen to be equal to the mean value of the open circuit voltage $\overline{V_{oc}}$. The reference intensity $I_{PL,ref}$ is thus equal to the photoluminescence intensity associated with (or coupled to) the reference voltage $V_{oc,ref}$ here equal to $\overline{V_{oc}}$, on the curve $C_1$. In a variant, the reference voltage $V_{oc,ref}$ could be any one of the voltage values $V_{oc}$ between the mean $\overline{V_{oc}}$ increased by two times the standard deviation σ and the mean $\overline{V_{oc}}$ decreased by two times the standard deviation σ, that is, within the interval [$\overline{V_{oc}}$−2σ; $\overline{V_{oc}}$+2σ].

Figure 2:
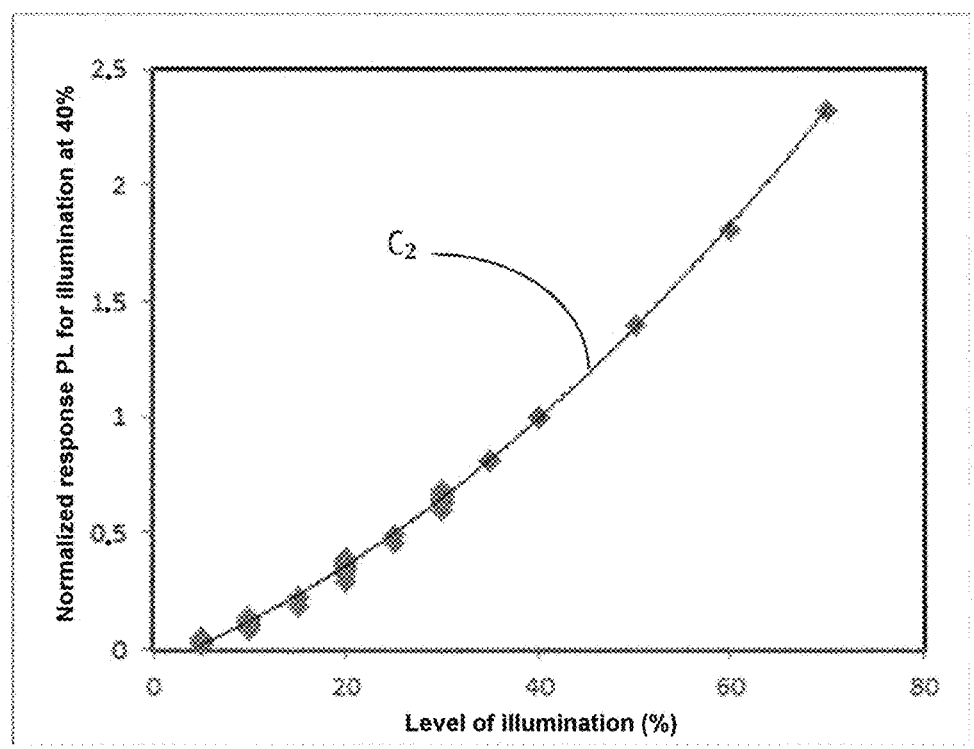
FIG. 2 shows data on the change in the luminescence response of a photovoltaic cell as a function of an applied excitation level, the intensity being normalized for a chosen excitation level.

The method then passes on to steps E08 to E011, enabling the determination of second change data regarding the photoluminescence response of a photovoltaic cell produced by the production line L as a function of the illumination level applied to that cell. By "photoluminescence response" is meant here the photoluminescence intensity of the photon signal emitted by the cell in response to an excitation. These second change data form a second curve, noted as $C_2$ such as is represented in FIG. 2. We note that the change curve $C_2$ can be determined from a single learning cell, or even several learning cells. In fact, the change in the photoluminescence response of a cell produced by the line L as a function of the illumination level is similar, or basically similar, from one cell to another, in particular regardless of the open circuit voltage of the cell. In the particular sample embodiment described here, steps E08 to E11 are carried out here for one learning cell, such as the cell $CLA_1$. In a variant, one could repeat these steps E08 to E011 for a limited number of learning cells.

Figure 5B:
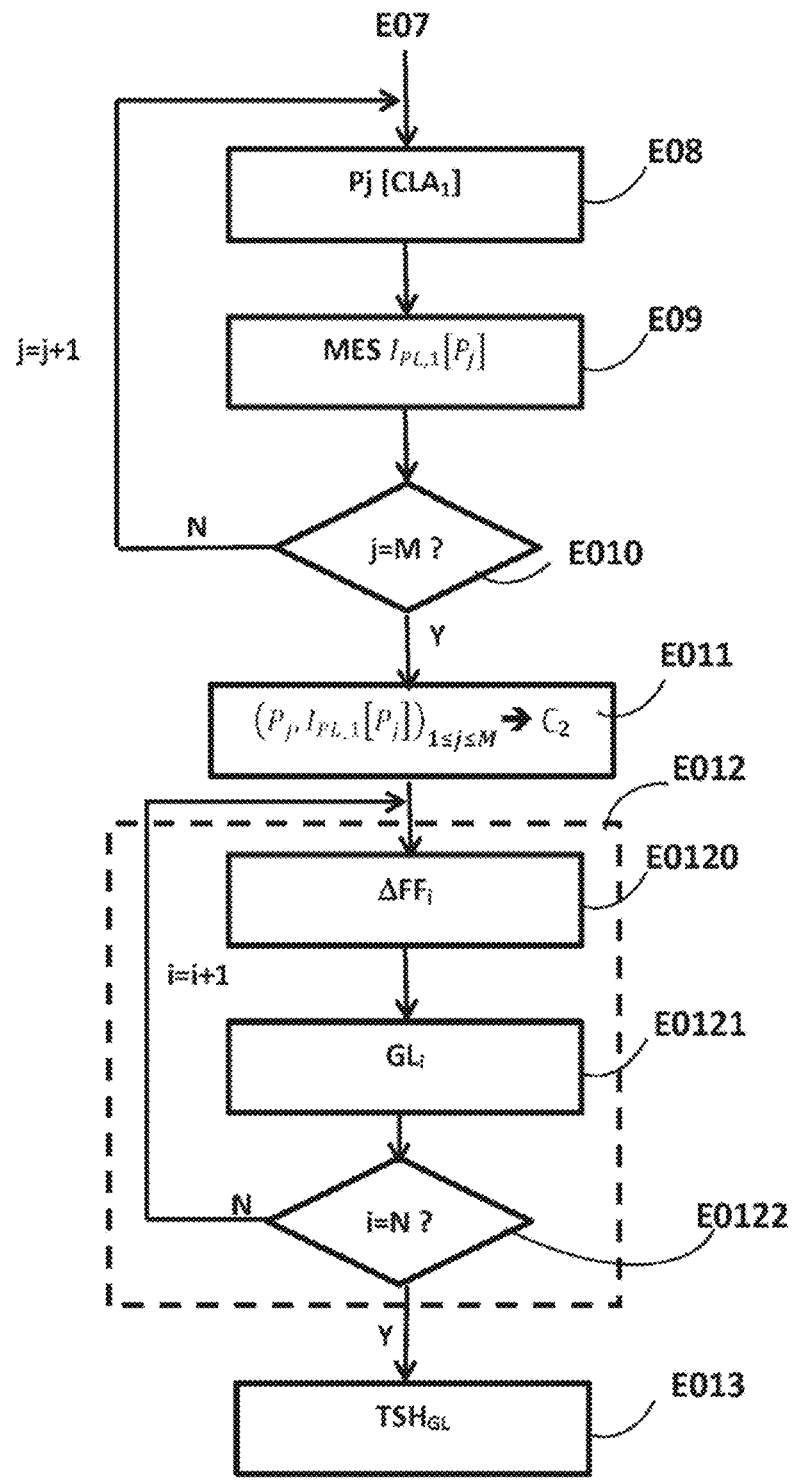

Referring to FIG. 5B, during step E08 one subjects the cell $CLA_1$ to a laser power level $P_j$, the index j being initially equal to 1. For example, the first laser power level $P_1$ applied corresponds to 10% of the maximum laser power emission of the laser device 1.

During a step E09, one measures the photoluminescence response of the cell $CLA_1$, that is, the luminescence intensity of the photon signal emitted by it, noted as $I_{PL\_1}[P_j]$, in response to the laser excitation of power $P_j$.

Steps E08 and E09 are repeated for a plurality of laser power levels, with j=1, 2, 3, . . . , M, ranging for example from 10% to around 80% of the maximum laser power of the laser 1. For example, one performs a dozen measurements of luminescence intensity $I_{PL\_1}[P_j]$ for a corresponding number of different laser power levels.

A test step E010 is provided so that the method returns to step E08 if the index j is less than M (branch N in FIG. 5B). When the photoluminescence response of the cell $CLA_1$ has been measured for the M levels of illumination $P_j$, with j=1, 2, 3, . . . , M, the method moves on to step E011 (branch Y in FIG. 5B).

At the end of step E010, once the steps E08 and E09 have been repeated M times, one obtains M pairs of values ($P_j$, $I_{PL\_1}[P_j]$), with j=1, 2, 3, . . . , M.

During step E011, using the M pairs of values ($P_j$, $I_{PL\_1}[P_j]$) the control device 4 determines the second data on the change in photoluminescence intensity of a photovoltaic cell produced by the production line L as a function of the level of illumination. These second change data form the curve $C_2$, as represented in FIG. 2. This curve $C_2$ is the same, or essentially the same, for all the cells produced by the production line L, regardless of their respective values $V_{oc}$. In the case represented in FIG. 2, the curve C2 can be adjusted by a polynomial law of the type $$\frac{I_{PL\_2}[P_j]}{I_{PL\_2}[P=40\%]} = a + b \cdot P_j + c \cdot P_j^2 + \ldots$$

The learning phase thus lets one determine the change curves $C_1$ and $C_2$ based on the learning data (that is, measurement data regarding the learning cells) and it can be performed the first time the production line L is placed in service.

The learning phase also includes steps E012 and E013 making it possible to determine a critical threshold of the defect quantification parameter $TSH_{GL}$. These steps E012 and E013 shall be described further below.

Quality Monitoring

We shall now describe the phase of quality monitoring of photovoltaic cells produced by the production line L which is carried out after the learning phase. We shall note as $CLC_k$, with k=1, 2, . . . , a set of photovoltaic cells to be monitored.

In the particular embodiment described here, the quality monitoring is performed for each cell to be monitored $CLC_k$, prior to the end of the manufacturing process of the cell, and more precisely prior to its metallization.

The quality monitoring involves, for each cell to be monitored $CLC_k$:

a preliminary step E2 of determination of an excitation level adjusted to the cell to be monitored $CLC_k$;
an excitation step E3, during which said cell $CLC_k$ is subjected to an excitation at an adjusted excitation level;
a step E4 of acquisition of at least one luminescence image of the cell $CLC_k$ after excitation;
a step E5 of processing of the acquired image.

Adjustment of the Excitation Level:

The preliminary step E2 consists in determining an excitation level, in the present case a level of illumination, adjusted to said cell $CLC_k$. By definition, an excitation level "adjusted" to a photovoltaic cell is an excitation level adapted so that the luminescence intensity $I_{PL,k}$ of the photon signal emitted by the cell in question in response to the applied excitation level is equal to the reference intensity $I_{PL,ref}$. We note as $P[CLC_k]$ the excitation level adjusted to the cell $CLC_k$, corresponding here to a level of illumination defined by a percentage of the maximum emission power of the laser emission device 1.

Figure 6A:
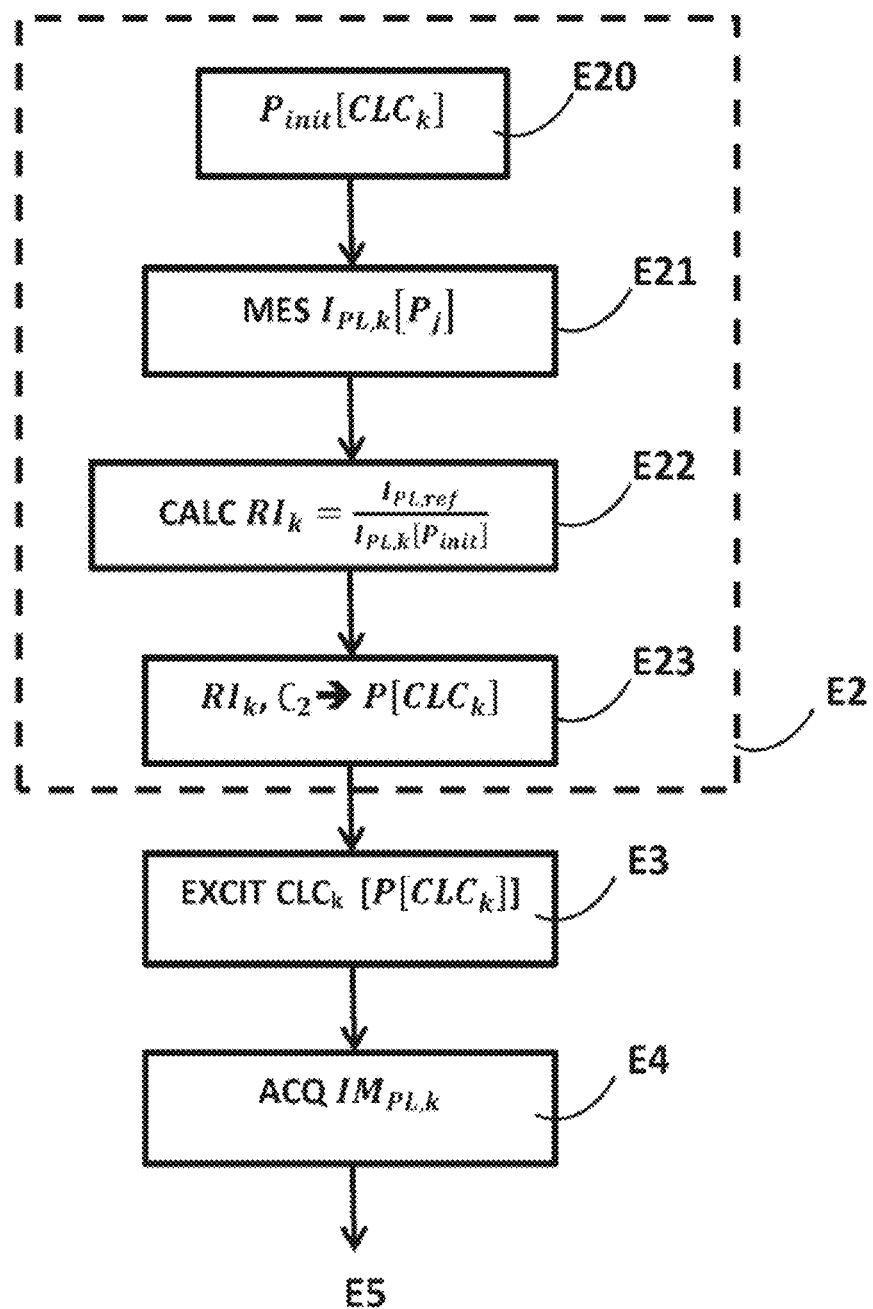
FIGS. 6A and 6B show the steps of one quality monitoring phase of the method of the invention, according to one particular embodiment.

Step E2 includes the substeps E20 to E23 described below, referring to FIG. 6A.

Substep E20 consists in subjecting the cell to be monitored $CLC_k$ to an initial chosen excitation level $P_{init}$ with the aid of the laser emission device 1. The initial excitation level $P_{init}$ corresponds to a level of illumination, equal here to 40% of the maximum laser emission power of the laser device 1.

The sensor 2 measures the photoluminescence intensity $I_{PL,k}[P_{init}]$ of the photon signal emitted by the cell $CLC_k$ in response to the excitation $P_{init}$, during substep E21.

During substep E22, the control device 4 calculates a ratio of intensities between the reference value of the luminescence intensity and the measured value of the luminescence intensity, that is, between $I_{PL,ref}$ and $I_{PL,k}[P_{init}]$. We note this intensity ratio as $RI_k$:

$$RI_k = \frac{I_{PL,ref}}{I_{PL,k}[P_{init}]}$$

During a step E23, the control device 4 determines the excitation level $P[CLC_k]$ adjusted to the cell $CLC_k$ from the intensity ratio $RI_k$ and with the aid of the curve $C_2$.

This ratio of intensities $RI_k$ corresponds to a ratio of illumination levels constituting an adjustment factor $\alpha_k$ to be applied to the initial excitation level $P_{init}$ to obtain the excitation level $P[CLC_k]$ adjusted to the cell $CLC_k$.

In the particular embodiment described here, the curve $C_2$ is normalized for the initial chosen illumination level $P_{init}$. This means that the photoluminescence response at the illumination level defined by $P_{init}$ (here, 40%) is brought to 1 and that all of the points of the curve $C_2$ are adapted in similar fashion. Thanks to this, the adjusted illumination level $P[CLC_k]$ is given directly by the curve $C_2$ from the ratio $RI_k$ taken as the photoluminescence response. In other words, the illumination level adjusted to the cell $CLC_k$ is the illumination level on the curve $C_2$ associated with the photoluminescence response equal to the intensity ratio $RI_k$.

Let us take the example of a cell to be monitored, such as $CLC_1$, to which one applies an initial chosen illumination level $P_{init}$ equal to 40% of the maximum power of the laser emission device 1. Referring to FIG. 2, the photoluminescence intensity $I_{PL,1}[P_{init}]$ of the photon signal emitted by the cell $CLC_1$ in response to the illumination at $P_{init}$ (40%) is of the order of 40000 photons. The reference intensity $I_{PL,ref}$ being equal to 20000 photons in FIG. 2, the ratio of intensities $RI_1$ is equal to 0.5. On curve $C_2$, the normalized value of the photoluminescence response of 0.5 ($RI_1$) corresponds to an illumination level of 25% of the maximum laser power. One thus determines that the illumination level adjusted to the cell $CLC_1$ is equal to 25% of the maximum laser power.

Excitation

During the step of excitation E3, the cell to be monitored $CLC_k$ is subjected to an excitation at the adjusted excitation level as determined during step E2. In the particular example described here, the cell to be monitored $CLC_k$ is thus subjected to an adjusted illumination whose level is defined by the power $P[CLC_k]$ previously determined in step E2.

Acquisition

During step E4, the acquisition device 2 takes a photoluminescence image, noted as $IM_{PL,k}$, of the photoluminescence response of the cell $CLC_k$ after the excitation at the level of illumination $P[CLC_k]$. The photoluminescence image $IM_{PL,k}$ of said cell to be monitored $CLC_k$ is composed of a set of pixels $p_i$ associated with the respective luminescence intensity values, noted as $IM_{PL,k,i}$, i representing here a pixel index. In other words, a luminescence intensity $IM_{PL,k,i}$ is assigned to each image pixel $p_i$. We note as n the total number of pixels $p_i$ of an acquired photoluminescence image.

Image Processing

Figure 6B:
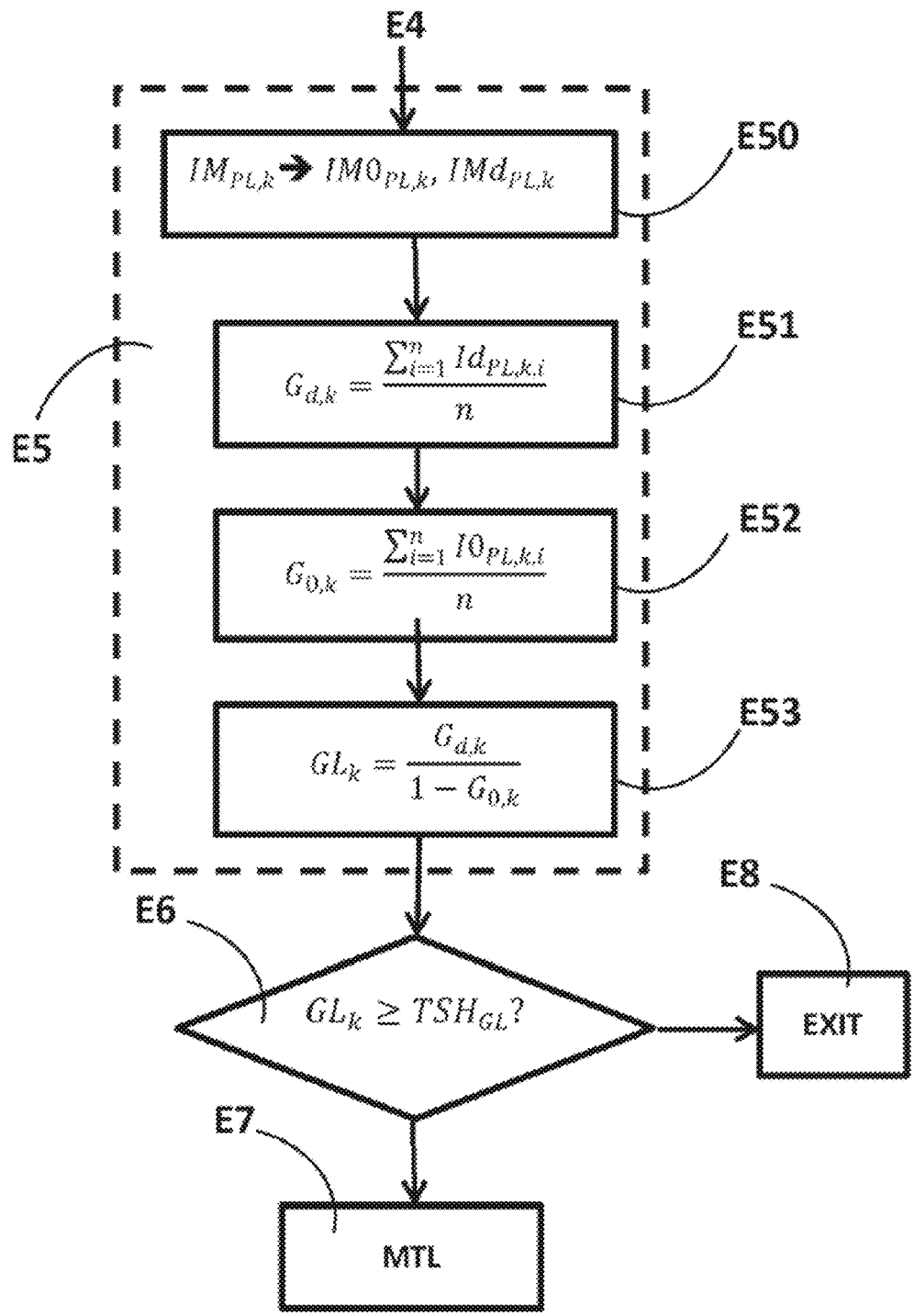

The control device 4 then carries out an image processing step E5 involving the substeps E50 to E53, described hereafter with reference to FIG. 6B. The image processing E5 makes it possible to determine a parameter $GL_k$ for quantification of the defects of the cell to be monitored $CLC_k$ from the photoluminescence image $IM_{PL,k}$.

During substep E50, the control device 4 decomposes the luminescence image $IM_{PL,k}$ of the cell to be monitored $CLC_k$ into a first image $IM0_{PL,k}$ corresponding to that cell without defects and a second image $IMd_{PL,k}$ corresponding to defects of that cell. Thus, one decouples the photoluminescence response of the cell $CLC_k$ from effects deriving from the presence of defects in the cell. The image $IM0_{PL,k}$ represents the background of the original image $IM_{PL,k}$ and corresponds to the photoluminescence response of the cell $CLC_k$ without defects.

In order to obtain the first image $IM0_{PL,k}$ one can decompose the original image $IM_{PL,k}$ for example by selecting N pixels of this original image. These N pixels can advantageously be situated at periodically spaced-apart locations. They form a matrix of pixels.

One then assigns to each of these N pixels a value which is representative of its direct local environment. The local environment of a given pixel is defined by a spatial zone containing that pixel, for example a square zone whose centre is the selected pixel. The size of this local environment zone is adapted to be larger than the current defects liable to involve the cell, which are generally well known.

The value assigned to each of the N selected pixels is the highest pixel value of the zone surrounding that pixel and constituting its local environment.

Next, one assigns a new value to each pixel of the image from the values assigned to the N selected pixels in order to obtain a first image corresponding to the cell without defects. Advantageously, the new values of the image pixels are determined by interpolation of the values assigned to the N selected pixels. In other words, by an interpolation calculation one reassigns a new value to each pixel of the image, except for the N pixels initially selected (which have the highest value of their environment). One thus obtains the first image $IM0_{PL,k}$ corresponding to that cell without defects.

Instead of assigning to each of the N selected pixels the highest pixel value of its local environment one could assign it a different value representative of its local environment, for example a mean of the pixel values of this local environment.

Next, one determines the second image $IMd_{PL,k}$ corresponding to the defects of that cell based on the luminescence image (or original image) $IM_{PL,k}$ and the first image $IM0_{PL,k}$. The second image $IMd_{PL,k}$ of the defects of the cell is obtained either by forming a ratio between the original image $IM_{PL,k}$ and the image without defects $IM0_{PL,k}$, or by performing a subtraction between the original image $IM_{PL,k}$ and the image without defects $IM0_{PL,k}$.

This method makes it possible to reconstruct the image by eliminating the zones where the photoluminescence response is weak, that is, zones considered to be defects, so as to obtain the first image $IM0_{PL,k}$ corresponding to the image of the cell without defects.

Each image ($IM_{PL,k}$, $IM0_{PL,k}$, $IMd_{PL,k}$) contains n respective pixels of index i and said pixels are assigned respective values of the luminescence intensity ($I_{PL,k,i}$, $I0_{PL,k,i}$, $Id_{PL,k,i}$).

During substep E51, the control device 4 calculates a mean value of the luminescence intensities assigned to the pixels of the image of defects $IMd_{PL,k}$, with the help of the following equation:

$$G_{d,k} = \frac{\sum_{i=1}^{n} Id_{PL,k,i}}{n} \quad (2)$$

where $Id_{PL,k,i}$ represents the photoluminescence intensity associated with a pixel of index i of the image $IMd_{PL,k}$;

n represents the total number of pixels in the particular image.

The result $G_{d,k}$ of equation (2) constitutes a first parameter for quantification of the defects of the cell to be monitored $CLC_k$.

During substep E52, the control device 4 calculates a mean value of the luminescence intensities associated with the pixels of the image without defect $IM0_{PL,k}$, with the help of the following equation:

$$G_{0,k} = \frac{\sum_{i=1}^{n} I0_{PL,k,i}}{n} \quad (3)$$

where $I0_{PL,k,i}$ represents the photoluminescence intensity associated with a pixel of index i of the image $IM0_{PL,k}$;

n represents the total number of pixels in the particular image.

During substep E53, the control device 4 corrects the first defect quantification parameter $G_{d,k}$ with the help of the mean $G_{0,k}$ by the following equation:

$$GL_k = \frac{G_{d,k}}{1 - G_{0,k}} \quad (4)$$

The result of this equation $GL_k$ constitutes the corrected parameter for quantification of the defects of the cell $CLC_k$.

The weighting of the parameter $G_{d,k}$ by the element $$\left(\frac{1}{1-G_{0,k}}\right)$$

makes it possible to correct for possible deviations caused by lack of precision in the adjusted illumination levels applied to the different cells. Ideally, the parameter $G_{0,k}$ is the same for all the cells to be monitored, inasmuch as the illumination levels have been regulated, or adjusted, so that the photoluminescence intensities are all identical (equal to the reference luminescence intensity $I_{PL,ref}$). However, in practice, the luminescence intensity $I_{PL,k}$ emitted by a cell to be monitored $CLC_k$ in response to an adjusted illumination level may deviate slightly with respect to the intended reference luminescence intensity $I_{PL,ref}$, for example because of a slight error in regulation of the laser emission device 1. This results in either an over-estimation or an under-estimation of the defect quantification parameter $G_{d,k}$, respectively in the case where $I_{PL,k}$ is greater than or less than $I_{PL,ref}$. The element $$\left(\frac{1}{1-G_{0,k}}\right)$$

constitutes a correction factor for the parameter $G_{d,k}$, making it possible to compensate for any deviations of the luminescence intensity of the cell to be monitored $CLC_k$.

Correlation Between Parameters GL and ΔFF

Figure 7:
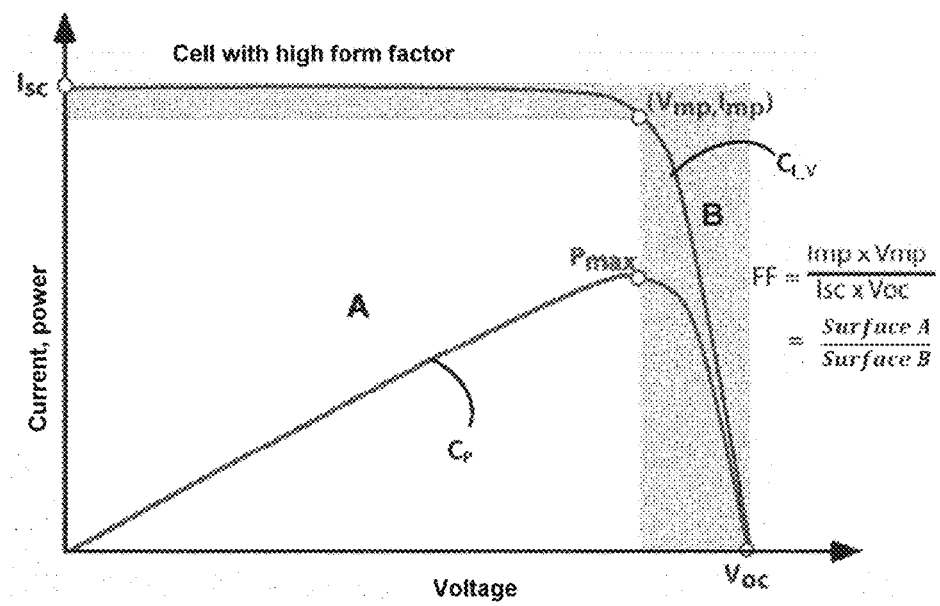
FIG. 7 shows the current/voltage and power/voltage characteristic curves of a photovoltaic cell.

FIG. 7 shows the current/voltage (curve $C_{I\_V}$) and power/voltage (curve $C_P$) characteristics of a photovoltaic cell. In this FIG. 7:

$I_{SC}$ represents the short circuit current of the cell, that is, the current flowing through the cell when the voltage on its terminals is zero (V=0);

$V_{OC}$ represents the open circuit voltage of the cell, that is, the voltage on the terminals of the cell when the current flowing is zero (I=0);

$I_{mp}$ and $V_{mp}$ represent, respectively, the current and the voltage of an operating point of the cell for which the power provided by it is at maximum.

By definition, the form factor of a photovoltaic cell is equal to $$FF = \frac{V_{mp} \cdot I_{mp}}{V_{OC} \cdot I_{SC}}$$

The form factor FF is the ratio between the maximum power provided by the cell and the ideal power which it would provide if it were perfect, without defect. This factor FF ultimately represents the degree of ideality of the cell and it constitutes a parameter indicative of the performance of the cell. Certain defects (for example, chemical impurities, microcracks, dislocations, etc.) are liable to occur in the cell during its manufacture and to cause a decrease in the form factor FF. We note as ΔFF a parameter of loss of form factor, representing an amplitude of decrease of the form factor.

As previously indicated, the learning phase of the method includes a step E012 of determination of a correlation between the parameters for quantification of defects $GL_i$ and the parameter of loss of form factor $\Delta FF_i$, for the learning cells $CLA_i$ (i ranging from 1 to N). This step E012 involves, for each learning cell $CLA_i$:

a first substep E0120 consisting in measuring a loss of form factor, or $\Delta FF_i$, for the cell $CLA_i$;

a second substep E0121 consisting in calculating the parameter $GL_i$ for the learning cell $CLA_i$.

The steps E0120 and E0121 are repeated for each of the learning cells (test E0122).

During step E0120, the loss of form factor $\Delta FF_i$ is evaluated for a finished learning cell, after metallization. For example, the loss of form factor $\Delta FF_i$ can be defined as a difference between the real form factor as measured for the cell $CLA_i$ and a reference form factor for the cell $CLA_i$. As a variant, one could use a more precise method of quantification of $\Delta FF_i$ taking into account various physical phenomena which impact the form factor (series resistance, shunt resistance, recombinations, etc.), as is described in the article "A Fill Factor Loss Analysis Method for Silicon Wafer Solar Cells" IEEE Journal of photovoltaics, Vol. 3, No. 4, October 2013, Digital Object Identifier 10.1109/JPHOTOV.2013.2270348.

The substep E0121 consists in carrying out step E5 of calculation of the defect quantification parameter $GL_i$ for the learning cell $CLA_i$, after having performed the steps E2 to E4 consisting in determining the illumination level adjusted to the cell $CLA_i$, exciting the cell $CLA_i$ with the initial chosen illumination level $P_{init}$ and acquiring a photoluminescence image of the cell $CLA_i$ in response to the adjusted illumination.

Figure 8:
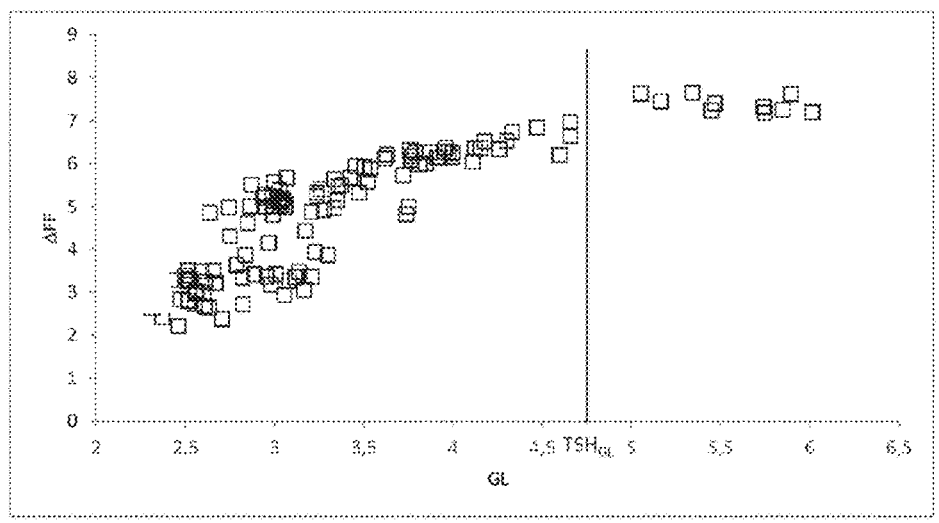
FIG. 8 shows data on the correlation between a parameter of loss of form factor and a parameter of quantification of the defects of a cell.

At the end of step E012, the device 4 saves the data on the change in the parameter of loss of form factor ΔFF as a function of the defect quantification parameter GL, as shown in FIG. 8.

During a step E013, the device 4 determines a critical threshold of the defect quantification parameter, noted as $TSH_{GL}$, beyond which the losses of form factor are estimated as being too large for the performance of the cell to be satisfactory. For example, referring to FIG. 8, this threshold $TSH_{GL}$ is set at 4.75. Of course, this threshold could be different to another cell production line.

Selection of the Monitored Cells $CLC_k$

The phase of quality monitoring of each cell to be monitored $CLC_k$ includes, after the step of determination of the parameter $GL_k$ of the cell (step E5), a test step E6 consisting in determining whether the performance of the cell $CLC_k$ is satisfactory. The test E6 consists in determining whether the defect quantification parameter $GL_k$ is greater than or equal to the critical threshold $TSH_{GL}$.

If the test is negative, the quality of the cell $CLC_k$ is judged satisfactory and the cell $CLC_k$ can move on to a next step in its manufacturing process, in the present case, a metallization step E7.

If the test is positive, the performance of the cell $CLC_k$ is considered to be unsatisfactory and the cell $CLC_k$ is removed from the production line L (step E8).

In the sample embodiment just described here, the quality monitoring method is carried out prior to the metallization step for the cell, which is carried out at the end of the manufacture. Thanks to this, the defective cells can be removed from the production line before metallization, which makes it possible to save on metal. However, one could contemplate the quality monitoring method being carried out at the end of the manufacture of the cells.

The different steps of the method are carried out by or under the control of the corresponding modules of the control device 4, in particular:

the learning module 40 is able to carry out the steps of the learning phase;

the module 41 for determination of excitation is able to carry out step E2 of determination of an excitation level;

the image processing module 42 is able to carry out the image processing step E5;

the cell selection module 44 is able to carry out steps E6 to E8.

In the particular embodiment just described, a learning phase is provided (steps E00 to E011), making it possible to determine the change curves $C_1$ and $C_2$, and then, for each cell $CLC_k$, a step E2 of determination of an excitation level $P[CLC_k]$ adjusted to the cell in question $CLC_k$.

In another particular embodiment, the cells $CLC_k$ are excited at a predefined, non-adaptive excitation level, which can be the same for all the cells. The excitation level of a cell to be monitored $CLC_k$ in this case is not adjusted to the cell in question. A typical excitation level is of the order of 1 sun. However, this excitation level can be lower or higher, in particular, between 0.1 and 10 suns. In this case, the method for monitoring the quality of the cells $CLC_k$ is similar to that just described, with the difference that it does not involve either a learning phase (steps E00 to E011) or a step (E2) of determination of an excitation level adjusted to each cell. The method according to this other embodiment involves, for each cell:

a step of excitation E3, during which the cell to be monitored $CLC_k$ is subjected to an excitation at a predefined excitation level (not specifically adjusted to the cell);

a step E4 of acquisition of at least one luminescence image $IM_{PL,k}$ of the cell to be monitored $CLC_k$ after excitation;

a step E5 of processing of the acquired image $IM_{PL,k}$.

During the processing step E5, the luminescence image of each cell to be monitored $CLC_k$ is decomposed into a first image corresponding to the cell without defects and a second image corresponding to the defects of said cell (step E50). A cell luminescence image being composed of a set of pixels to which respective values of luminescence intensity are assigned, in order to decompose the image $IM_{PL,k}$:

one selects a plurality N of pixels of said luminescence image $IM_{PL,k}$;

one assigns to each of the selected pixels a value which is representative of a local environment of said pixel;

one assigns a new value to each pixel of the image from the values of the selected pixels in order to obtain the first image $IM0_{PL,k}$;

one determines the second image $IMd_{PL,k}$, for example, by forming a ratio or a subtraction between the luminescence image of the cell $IM_{PL,k}$ and the first image $IM0_{PL,k}$.

The selected pixels of the luminescence image can be situated at periodically spaced-apart locations. The local environment of a selected pixel is a zone containing the selected pixel, for example, a square centred on it. The new value assigned to each pixel of the image is obtained, for example, by interpolation of the values of the selected pixels.

One then calculates (step E51) a mean of the luminescence intensity values associated with the pixels of the second image in order to determine a parameter for quantification of the defects of the cell, as previously explained.

For the implementing of this other embodiment, the monitoring system is similar to that previously described, with the difference that the control device 4 does not comprise either a learning module 40 or a module 41 for determination of an adjusted excitation level. Thus, the system comprises an excitation device adapted to apply an excitation to a cell to be monitored, a device for acquisition of a luminescence image of the cell after excitation and a control device comprising an image processing module 42, a module 43 for evaluation of a parameter of loss of form factor, and a cell selection module 44. The image processing module 42 is adapted to decompose the luminescence image of each cell to be monitored into a first image corresponding to the cell without defects and a second image corresponding to the defects of the cell, especially to select a plurality N of pixels of said luminescence image, assign to each of the selected pixels a value which is representative of a local environment of said pixel, assign a new value to each pixel of the image from the values of the selected pixels in order to obtain the first image, determine the second image from the luminescence image and the first image. Moreover, the image processing module can be adapted to calculate a mean of the luminescence intensity values associated with the pixels of the second image in order to determine a parameter for quantification of the defects of the cell.

The invention claimed is:

1. Method for monitoring the quality of a plurality of photovoltaic cells, the method comprising, for each cell:
    subjecting the cell to be monitored to an excitation;
    acquiring at least one luminescence image of the cell to be monitored after excitation; and
    processing the acquired image;
    wherein, for each cell to be monitored, the processing, comprises decomposing the luminescence image of the cell to be monitored into a first image corresponding to the cell without defects and a second image corresponding to defects of the cell,
    wherein the first image corresponds to the luminescence of the cell without defects taking into account the luminescence of a plurality of local areas of the cell, and
    wherein the second image is obtained based on the acquired luminescence image taking into account the first image.

2. The method according to claim 1, comprising, to decompose the luminescence image of the cell to be monitored, the luminescence image of the cell being composed of a set of pixels to which respective luminescence intensity values are assigned:
    selecting a plurality of pixels of said luminescence image;
    assigning to each of the selected pixels a value which is representative of a local environment of said pixel; and
    assigning a new value to each pixel of the image from the values of the selected pixels in order to obtain the first image corresponding to the cell without defects.

3. The method according to claim 2, comprising, in order to obtain the second image, calculating a mean of the luminescence intensity values associated with the pixels of the second image in order to determine a parameter for quantification of the defects of the cell.

4. The method according to claim 3, comprising correcting the defect quantification parameter by a correction factor determined from a mean of the pixel values of the first image.

5. The method according to claim 2, comprising in order to obtain the first image, assigning a new value to each pixel of the luminescence image by interpolation of the values of the selected pixels.

6. The method according to claim 2, wherein the selected pixels of the luminescence image are situated at periodically spaced-apart locations.

7. The method according to claim 1, comprising obtaining the second image by forming a ratio or a subtraction between the luminescence image of the cell and the first image.

8. System for monitoring the quality of a plurality of photovoltaic cells comprising hardware and software configured for implementing, for each cell:
subjecting the cell to be monitored to an excitation;
acquiring at least one luminescence image of the cell to be monitored after excitation, and
processing the acquired image;
wherein, for each cell to be monitored, the processing, comprises decomposing the luminescence image of the cell to be monitored into a first image corresponding to the cell without defects and a second image corresponding to defects of the cell,
wherein the first image corresponds to the luminescence of the cell without defects taking into account the luminescence of a plurality of local areas of the cell, and
wherein the second image is obtained based on the acquired luminescence image taking into account the first image.

9. System for monitoring the quality of a plurality of photovoltaic cells comprising:
an excitation device adapted to apply an excitation to a cell to be monitored;
an acquisition device for acquisition of a luminescence image of the cell after excitation; and
an image processing module;
wherein the image processing module is adapted to decompose the luminescence image of each cell to be monitored into a first image corresponding to that cell without defects and a second image corresponding to defects of that cell,
wherein the first image corresponds to the luminescence of the cell without defects taking into account the luminescence of a plurality of local areas of the cell, and
wherein the second image is obtained based on the acquired luminescence image taking into account the first image.

10. The system according to claim 9, wherein the image processing module is designed to select a plurality of pixels of said luminescence image, assign to each of the selected pixels a value which is representative of a local environment of said pixel, and assign a new value to each pixel of the image from the values of the selected pixels in order to obtain the first image.

11. The system according to claim 10, wherein the image processing module is designed, in order to obtain the second image, to calculate a mean of the luminescence intensity values associated with the pixels of the second image in order to determine a parameter for quantification of the defects of the cell.

12. The system according to claim 11, wherein the image processing module is designed to correct the defect quantification parameter by a correction factor determined from a mean of the pixel values of the first image.

13. The system according to claim 10, wherein the image processing module is designed, in order to obtain the first image, to assign a new value to each pixel of the luminescence image by interpolation of the values of the selected pixels.

14. The system according to claim 10, wherein the image processing module is designed to situate the selected pixels of the luminescence image at periodically spaced-apart locations.

15. The system according to claim 9, wherein the image processing module is designed to obtain the second image by forming a ratio or a subtraction between the luminescence image of the cell and the first image.

* * * * *